(12) United States Patent
Gourlaouen

(10) Patent No.: US 7,276,086 B2
(45) Date of Patent: Oct. 2, 2007

(54) COMPOSITION COMPRISING AT LEAST ONE PYRAZINE DERIVATIVE AND THE USE THEREOF FOR THE DIRECT OR OXIDATION DYEING AND/OR OPTICAL BLEACHING OF KERATIN FIBERS

(76) Inventor: Luc Gourlaouen, 3, rue Jean-Jacques Rousseau, F-92600 Asniére (FR)

( * ) Notice: Subject to any disclaimer, the term of this patent is extended or adjusted under 35 U.S.C. 154(b) by 180 days.

(21) Appl. No.: 10/490,860

(22) PCT Filed: Sep. 24, 2002

(86) PCT No.: PCT/FR02/03251

§ 371 (c)(1), (2), (4) Date: Mar. 26, 2004

(87) PCT Pub. No.: WO03/028684

PCT Pub. Date: Apr. 10, 2003

(65) Prior Publication Data

US 2004/0237215 A1    Dec. 2, 2004

(30) Foreign Application Priority Data

Sep. 28, 2001  (FR)  .................................. 01 12532

(51) Int. Cl.
  *A61K 7/13*  (2006.01)
(52) U.S. Cl. ...................... 8/405; 8/406; 8/409; 8/410; 8/411; 8/421; 8/425; 8/567; 8/573; 544/224
(58) Field of Classification Search ...................... 8/405, 8/406, 409, 410, 411, 421, 425, 567, 573; 544/224

See application file for complete search history.

(56) References Cited

U.S. PATENT DOCUMENTS

| | | | |
|---|---|---|---|
| 3,429,646 A | 2/1969 | Steed | 8/10 |
| 3,808,209 A * | 4/1974 | Donald | 544/336 |
| 4,823,985 A | 4/1989 | Grollier et al. | 222/1 |
| 5,708,151 A | 1/1998 | Möckli | 534/608 |
| 5,792,221 A | 8/1998 | Lagrange et al. | 8/415 |
| 5,968,206 A | 10/1999 | Audousset et al. | 8/409 |
| 6,077,320 A | 6/2000 | Andrean et al. | 8/405 |
| 6,383,230 B1 | 5/2002 | Genet et al. | 8/405 |

FOREIGN PATENT DOCUMENTS

| | | |
|---|---|---|
| DE | 199 33 187 | 1/2001 |
| EP | 0 714 954 B1 | 6/1996 |
| FR | 1 463 870 | 11/1966 |
| FR | 2 586 913 | 3/1987 |
| FR | 2 692 572 | 12/1993 |
| JP | 8-231358 | 9/1996 |
| JP | 2000-230133 | 8/2000 |
| WO | WO95/01772 | 1/1995 |
| WO | WO95/15144 | 6/1995 |
| WO | WO 02/072583 | 9/2002 |

OTHER PUBLICATIONS

Jae-yun Jaung et al. Syntheses and Characterization of New Styryl Fluoresent Dyes from DAMN Part II, Dyes and Pigments, vol. 34, No. 4, 1997, pp. 255-266.*
Kazuko Shiral, Lourmal of the Society of Dyes and Colorists, vol. 114, No. 12, Dec. 1998, pp. 368-374.*
StIC Search Report Mar. 23, 2006.*
Chemical Abstracts, vol. 127, No. 20, Nov. 17, 1997, Columbus, Ohio, US; abstract No. 278212t.
Jae-yun Jaung et al., "Synthesis and Characterization of New Styryl Fluorescent Dyes from DAMN. Part II," Dyes and Pigments, vol. 34, No. 4, 1997, pp. 255-266.
Natu R. Patel, Journal of Heterocyclic Chemistry, vol. 3, No. 4, 1966, pp. 512-517.
Kazuko Shirai, Journal of the Society of Dyes and Colorists, vol. 114, No. 12, Dec. 1998, pp. 368-374.

* cited by examiner

*Primary Examiner*—Eisa Elhilo
(74) *Attorney, Agent, or Firm*—Finnegan, Henderson, Farabow, Garrett and Dunner, LLP

(57) ABSTRACT

The invention relates to a composition comprising a pyrazine derivative and to methods using said compositions as an optical bleach and/or dye in a direct or oxidation dyeing composition for keratin fibers, such as human keratin fibers, for example, hair. The invention also relates to methods of making said compositions and to a multicompartment device for dyeing and/or optical bleaching containing the claimed composition.

43 Claims, No Drawings

COMPOSITION COMPRISING AT LEAST ONE PYRAZINE DERIVATIVE AND THE USE THEREOF FOR THE DIRECT OR OXIDATION DYEING AND/OR OPTICAL BLEACHING OF KERATIN FIBERS

The invention relates to a composition containing a pyrazine derivative, the use of said derivative as an optical bleach and/or dye in a direct or oxidation dyeing composition for keratin fibers, in particular human keratin fibers and more particularly the hair.

The subject of the invention is also the methods using these compositions.

There are mainly two major types of hair dyeing.

The first is semi-permanent dyeing or direct dyeing, which uses dyes capable of giving the hair's natural color a more or less pronounced modification that withstands shampooing several times. These dyes are known as direct dyes and may be used in two different ways. The colorations may be performed by applying the composition containing the direct dye(s) directly to the keratin fibers, or by applying a mixture, prepared extemporaneously, of a composition containing the direct dye(s) with a composition containing an oxidizing bleaching agent, which is preferably aqueous hydrogen peroxide solution. Such a method is then termed "bleaching direct dyeing".

The second is permanent dyeing or oxidation dyeing. This is performed with "oxidation" dye precursors, which are colorless or weakly colored compounds which, once mixed with oxidizing products, at the time of use, can give rise to colored compounds and dyes via a method of oxidative condensation. It is often necessary to combine one or more direct dyes with the oxidation bases and couplers in order to neutralize or attenuate the shades with too much of a red, orange or golden glint or, on the contrary, to accentuate these red, orange or golden glints.

Among the available direct dyes, nitrobenzene direct dyes are not sufficiently strong, and indoamines, quinone dyes and natural dyes have low affinity for keratin fibers and consequently lead to colorations that are not sufficiently fast with respect to the various treatments to which the fibers may be subjected, and in particular with respect to shampooing.

In addition, there is a need to obtain a bleaching effect on keratin fibers. This bleaching is conventionally obtained via a method of bleaching the melanins of the hair via an oxidizing system generally consisting of hydrogen peroxide optionally combined with persalts. This bleaching system has the drawback of degrading the keratin fibers and of impairing their cosmetic properties.

The Applicant thus investigated compounds that can provide solutions to the problems mentioned above, i.e. that have good dyeing affinity for keratin fibers, good fastness properties with respect to external agents, and in particular with respect to shampooing, and that also allow optical bleaching to be obtained without impairing the fiber.

As a result of these investigations, the Applicant has now discovered, surprisingly, and unexpectedly, that the use of pyrazine derivatives of formula (I) defined below allow these objectives to be achieved.

A first subject of the present invention is therefore a composition to be applied to keratin fibers, in particular human keratin fibers and more particularly the hair, characterized in that it comprises, in an appropriate medium, at least one pyrazine derivative of the following formula (I):

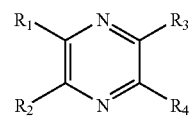

or their addition salts with an acid or with an alkaline agent, in which formula (I):

$R_1$ and $R_2$, which may be identical or different, are chosen from the group consisting of a hydrogen atom, a cyano radical, a hydroxyl radical, an alkyl radical, an alkenyl radical, an alkoxy radical, a halogen atom, an amino radical, a radical NRaRb, a COOX radical, or form, together with the two carbon atoms of the pyrazine ring carrying them, a mono- or polycyclic heterocycle comprising one or more heteroatoms which are unsubstituted or substituted with one or more alkyl radicals, aryl radicals, cyano radicals, halogen atoms, amino radicals or radicals NRcRd, $R_3$ and $R_4$, which may be identical or different, are chosen from the group consisting of a hydroxyl radical, a cyano radical, a halogen atom, an amino radical, a radical NReRf, a COOX radical, an alkyl radical, an alkenyl radical, an alkoxy radical, or form, together with the two carbon atoms of the pyrazine ring carrying them, a mono- or polycyclic heterocycle comprising one or more heteroatoms which are unsubstituted or substituted with one or more alkyl radicals, aryl radicals, cyano radicals, halogen atoms, amino radicals or radicals NRgRh, it being possible for the alkyl, alkoxy and alkenyl radicals in $R_1$ to $R_4$ to be substituted with one-or more hydroxyl radicals, amino radicals, aryl radicals, or a monocyclic or fused heterocycle, X denotes a hydrogen atom, or an alkyl radical, or an ion derived from an alkali or alkaline-earth metal or from an organic amine or an ammonium ion, Ra, Rb, Rc, Rd, Re, Rf, Rg and Rh denote, independently of each other, an alkyl or aryl radical, or form, with the nitrogen atom carrying them, a 5- or 6-membered heterocycle which may comprise one or more other heteroatoms, and which may be substituted with one or more alkyl radicals, aryl radicals or halogen atoms.

For the purposes of the present invention, the term "alkyl" means a linear, cyclic or branched, saturated chain comprising from 1 to 10 carbon atoms, and preferably from 1 to 4 carbon atoms, which may be interrupted by one or more heteroatoms and which may be substituted with one or more hydroxyl radicals, halogen atoms, amino radicals, aryl radicals or heterocyclic radicals.

For the purposes of the present invention, the term "alkenyl" means an unsaturated chain comprising one or more linear, cyclic or branched unsaturations, comprising from 1 to 10 carbon atoms, and preferably from 2 to 5 carbon atoms, which may be interrupted by one or more heteroatoms, and which may be substituted with one or more hydroxyl radicals, halogen atoms, amino radicals, aryl radicals or heterocyclic radicals.

For the purposes of the present invention, the term "aryl" means an aromatic system comprising from 6 to 30 carbon atoms, consisting of a single ring or of several fused rings, and which may be substituted with one or more hydroxyl radicals, halogen atoms, amino radicals or alkyl radicals.

For the purposes of the present invention, the term "alkoxy" means an O-alkyl radical in which the alkyl has the same meaning as indicated above.

For the purposes of the present invention, the term "heterocycle" means a saturated or unsaturated mono- or polycyclic linkage comprising at least one heteroatom, which may be condensed with an aryl radical and which may be substituted on the carbon atoms or on the heteroatoms with one or more hydroxyl radicals, halogen atoms, amino radicals or aryl radicals.

According to the present invention, at least one of the substituents $R_1$ to $R_3$ preferably denotes a cyano or amino radical and/or $R_3$ and $R_4$ form an optionally substituted heterocycle.

As compounds of formula (I), mention may be made for example of 5-chloro-8-benzylaminopyrazino[2,3-d]pyridazine, 2,3-dicyano-5-hydroxy-6-[2-julolidinylethenyl]pyrazine and 2,3-bis[2-(2-pyridinyl)ethenyl]-5,6-dicyanopyrazine, corresponding to the following formulae:

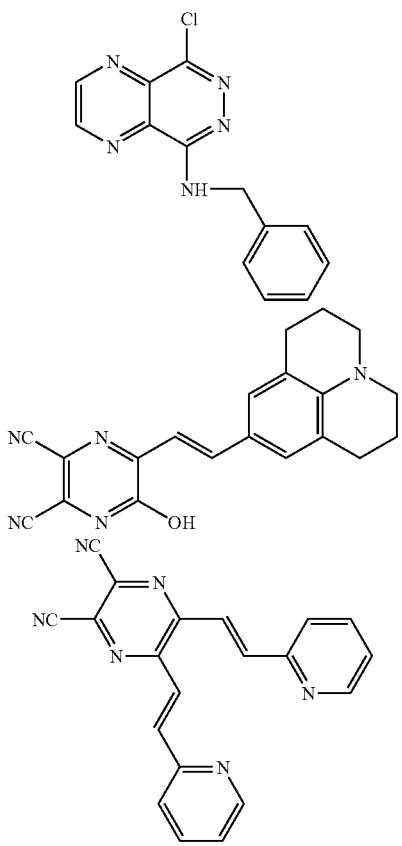

The compounds of formula (I) are known compounds whose synthesis is for example described in the following references: Natu R. PATEL, Journal of Heterocyclic Chemistry Vol. 3, No. 4, 1966, pp. 512-517. Kazuko SHIRAI, Journal of the Society of Dyes and Colorists Vol. 114, No. 12, December 1998, pp. 368-374.

The compound(s) of formula (I) preferably represent(s) from 0.0005% to 12% by weight approximately relative to the total weight of the composition according to the invention, and even more preferably from 0.005% to 6% by weight approximately relative to this weight.

The appropriate medium for application to keratin fibers, in particular human keratin fibers and more particularly the hair, generally consists of water or a mixture of water and of at least one organic solvent.

Examples of organic solvents that may be mentioned include $C_1$-$C_4$ lower alkanols such as ethanol and isopropanol; glycerol; glycols and glycol ethers, for instance 2-butoxyethanol, propylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvents may be present in proportions preferably of between 1% and 40% by weight approximately and even more preferably between 5% and 30% by weight approximately relative to the total weight of the dye composition.

The pH of the composition in accordance with the invention is generally between 3 and 12 approximately and preferably between 5 and 11 approximately. It may be adjusted to the desired value by means of acidifying or basifying agents usually used in the dyeing of keratin fibers.

Examples of acidifying agents that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (II) below:

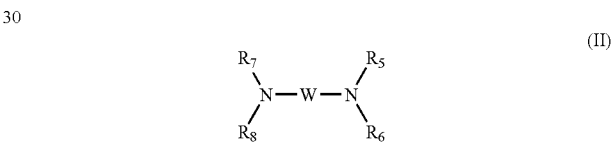

in which W is a propylene residue optionally substituted with a hydroxyl group or a $C_1$-$C_6$ alkyl radical; $R_5$, $R_6$, $R_7$ and $R_8$, which may be identical or different, represent a hydrogen atom or a $C_1$-$C_6$ alkyl or $C_1$-$C_6$ hydroxyalkyl radical.

According to one preferred embodiment, the composition in accordance with the invention may comprise, in addition to the compound(s) of formula (I), one or more additional direct dyes of nonionic, cationic or anionic nature, which may be chosen, for example, from the following red or orange benzene dyes:
-1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)-aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene, 2-nitro-4'-hydroxydiphenylamine, and
1-amino-2-nitro-4-hydroxy-5-methylbenzene.

The composition in accordance with the invention may also comprise, in addition to or as replacement for these benzene dyes, one or more additional direct dyes chosen from yellow, green-yellow, blue or violet benzene dyes, azo dyes, anthraquinone dyes, naphthoquinone dyes, benzoquinone dyes, indigoid dyes, and triarylmethane-based dyes.

These additional direct dyes may especially be basic dyes, among which mention may be made more particularly of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which mention may be made more particularly of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in WO 95/01772, WO 95/15144 and EP-A-0 714 954, the content of which forms an integral part of the present invention.

Among the additional yellow and green-yellow benzene direct dyes that may be mentioned, for example, are the compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β, γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue or violet benzene direct dyes that may be mentioned, for example, are the compounds chosen from:

1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene,
1-(β, γ-dihydroxypropyl)amino-4-(N-ethyl-N-β-hydroxyethyl)amino-2-nitrobenzene,
2-nitro-para-phenylenediamines having the following formula (III):

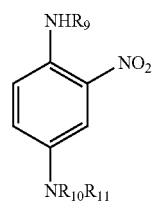

in which:
$R_{10}$ represents a $C_1$-$C_4$ alkyl radical or a β-hydroxyethyl, β-hydroxypropyl or γ-hydroxypropyl radical;
$R_9$ and $R_{11}$, which may be identical or different, represent a β-hydroxyethyl, β-hydroxypropyl, γ-hydroxypropyl or β, γ-dihydroxypropyl radical, at least one of the radicals $R_{10}$, $R_{11}$ or $R_9$ representing a γ-hydroxypropyl radical and $R_{10}$ and
$R_{11}$ not simultaneously being able to denote a β-hydroxyethyl radical when $R_{10}$ is a γ-hydroxypropyl radical, such as those described in FR 2 692 572.

When they are present, the additional direct dye(s) preferably represent(s) from 0.0005% to 12% by weight approximately relative to the total weight of the composition, and even more preferably from 0.005% to 6% by weight approximately relative to this weight.

When it is intended for oxidation dyeing, the composition in accordance with the invention comprises, in addition to the compound(s) of formula (I), at least one oxidation base chosen from the oxidation bases conventionally used for oxidation dyeing and among which mention may be made especially of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy) pyrrolidine, and the addition salts thereof with an acid or with an alkaline agent.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines that may be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned more particularly, for example, are pyridine derivatives, pyrimidine derivatives and pyrazole derivatives, and the addition salts thereof with an acid or with an alkaline agent.

When they are used, the oxidation base(s) advantageously represent(s) from 0.0005% to 12% by weight relative to the total weight of the composition and even more preferably from 0.005% to 6% by weight approximately relative to this weight.

When it is intended for oxidation dyeing, the composition in accordance with the invention may also comprise, in addition to the compounds of formula (I) and the oxidation bases, at least one coupler so as to modify or to enrich with glints the shades obtained using the compounds of formula (I) and the oxidation base(s).

The couplers that may be used in the composition in accordance with the invention may be chosen from the couplers conventionally used in oxidation dyeing, and among which mention may be made especially of meta-phenylenediamines, meta-amino-phenols, meta-diphenols and heterocyclic couplers, and the addition salts thereof with an acid or with an alkaline agent.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the coupler(s) preferably represent(s) from 0.0001% to 10% by weight and even more preferably from 0.005% to 5% by weight approximately relative to the total weight of the composition.

In general, the addition salts with an acid that may be used in the context of the compositions of the invention (compounds of formula (I), oxidation bases and couplers) are chosen especially from the hydrochlorides, hydrobromides, sulfates, citrates, succinates, tartrates, tosylates, benzenesulfonates, lactates and acetates.

The addition salts with an alkaline agent that may be used in the context of the compositions of the invention (compounds of formula (I), oxidation bases and couplers) are chosen especially from the addition salts with alkali metals or alkaline-earth metals, with ammonia and with organic amines, including alkanolamines and the compounds of formula (II).

The composition in accordance with the invention may also comprise various adjuvants conventionally used in compositions, intended to be applied to the hair, such as anionic, cationic, nonionic, amphoteric or zwitterionic surfactants or mixtures thereof, anionic, cationic, nonionic, amphoteric or zwitterionic polymers, or mixtures thereof, mineral or organic thickeners, antioxidants, penetrating agents, sequestering agents, fragrances, buffers, dispersants, conditioners, for instance, volatile or nonvolatile, modified or unmodified silicones, film-forming agents, ceramides, preserving agents and opacifiers.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of liquids, shampoos, creams or gels, or in any other suitable form.

When one or more oxidation bases are used, optionally in the presence of one or more couplers, or when the compound(s) of the invention of formula (I) is(are) used in the context of a bleaching direct dyeing operation, then the composition in accordance with the invention may also contain at least one oxidizing agent chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide or of enzymes is particularly preferred.

A subject of the invention is also the use of the compounds of formula (I) as defined above, as a direct dye and/or optical bleaching agent in, or for the manufacture of, a composition for dyeing keratin fibers, in particular human keratin fibers and more particularly the hair.

Another subject of the invention is a method for dyeing and/or optical bleaching of keratin fibers, in particular human keratin fibers and more particularly the hair, using a composition as defined above, in the absence of oxidation dyes and of oxidizing agents.

Another subject of the invention is a method for dyeing keratin fibers, in particular human keratin fibers and more particularly the hair using a composition as defined above, in the absence of oxidation dyes but in the presence of oxidizing agents.

According to a first variant of these dyeing methods in accordance with the invention, at least one composition as defined above is applied to the fibers, for a time that is sufficient to develop the desired coloration or optical bleaching, after which the fibers are rinsed, optionally washed with shampoo, rinsed again and dried.

According to a second variant of these dyeing methods in accordance with the invention, at least one composition as defined above is applied to the fibers, for a time that is sufficient to develop the desired coloration or optical bleaching, without final rinsing.

According to a third variant of the dyeing method in accordance with the invention, the dyeing method comprises a preliminary step that consists in separately storing, on the one hand, a composition comprising, in a medium that is suitable for dyeing, at least one compound of formula (I) as defined above, and, on the other hand, a composition comprising, in a medium that is suitable for dyeing, at least one oxidizing agent, and then in mixing them together at the time of use, followed by applying this mixture to the fibers for a time that is sufficient to develop the desired coloration, after which the fibers are rinsed, optionally washed with shampoo, rinsed again and dried.

Another subject of the invention is a method for the oxidation dyeing of keratin fibers, and in particular human keratin fibers such as the hair using a composition as defined above in the presence of oxidation dyes.

According to this dyeing method, the dyeing method comprises a preliminary step that consists in separately storing, on the one hand, a composition comprising, in a medium that is suitable for dyeing, at least one compound of formula (I) as defined above and at least one oxidation base, and, on the other hand, a composition comprising, in a medium that is suitable for dyeing, at least one oxidizing agent, and then in mixing them together at the time of use, followed by applying this mixture to the fibers for a time that is sufficient to develop the desired coloration, after which the fibers are rinsed, optionally washed with shampoo, rinsed again and dried.

Another subject of the invention is a multi-compartment device for dyeing and/or optical bleaching of keratin fibers, in particular human keratin fibers and more particularly the hair, comprising at least one compartment containing a composition comprising at least one pyrazine derivative of formula (I) as defined in the invention, and at least one other compartment containing a composition comprising at least one oxidizing agent. This device may be equipped with a means for applying the desired mixture to the hair, such as the devices described in patent FR-2 586 913 in the name of the Applicant.

The time required to develop the coloration or to obtain the optical bleaching effect on the keratin fibers is generally between 3 and 60 minutes and even more precisely 5 and 40 minutes.

The temperature required to develop the coloration or to obtain the optical bleaching effect on the keratin fibers is generally between room temperature and 80° C. and even more precisely 15 and 40° C.

The examples that follow are intended to illustrate the invention without, however, limiting its scope.

EXAMPLES 1 and 2

The following direct dyeing compositions were prepared (contents in grams):

| EXAMPLES | 1 | 2 |
|---|---|---|
| 5-chloro-8-benzylaminopyrazino[2,3-d]-pyridazine (compound of formula (I)) | 0.5 | — |
| 2,3-dicyano-5-hydroxy-6-(2-julolidinyl-ethenyl)pyrazine (compound of formula (I)) | — | 0 5 |

| EXAMPLES | 1 | 2 |
|---|---|---|
| Common dye carrier | () | () |
| Demineralized water qs | 100 g | 100 g |

(**) Common dye carrier:
| | |
|---|---|
| Benzyl alcohol | 8 g |
| Polyethylene glycol 400 | 12 g |
| Hydroxymethylcellulose | 1.6 g |
| Alkyl polyglucoside as an aqueous solution containing 60% active material (AM) | 6 g AM |
| Preservatives | 0.12 g |

Locks of natural gray hair which is 90% white were immersed at room temperature (about 20° C.) in each of the dyeing compositions described above for 20 minutes. The hair was then rinsed and dried.

The locks were dyed with the composition of example 1 in an orange-red shade.

The locks were dyed with the composition of example 2 in a yellow shade.

The invention claimed is:

1. A composition for treating human keratin fibers comprising:
an appropriate medium for treating human keratin fibers, wherein said medium is water or a mixture of water and at least one organic solvent and,
at least one compound comprised in said medium, wherein said compound is chosen from pyrazine derivatives of formula (I) and addition salts thereof with an acid or with an alkaline agent:

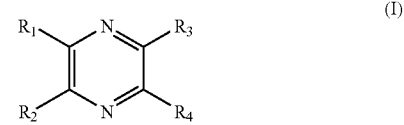

wherein:
$R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;
$R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms.

2. The composition according to claim 1, wherein at least one of the substituents $R_1$ to $R_3$ is chosen from cyano and amino radicals.

3. The composition according to claim 1, wherein $R_3$ and $R_4$ form an optionally substituted heterocycle.

4. The composition according to claim 1, wherein the at least one compound is chosen from those of the following formulae:

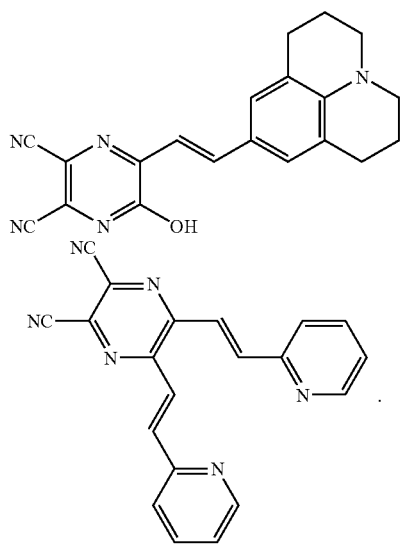

5. The composition according to claim 1, wherein the at least one compound has the following structure:

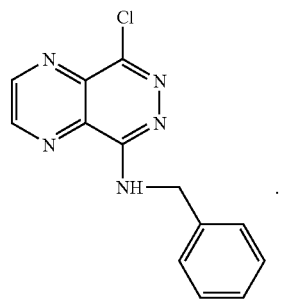

6. The composition according to claim 1, wherein the at least one compound is present in an amount ranging from 0.0005% to 12% by weight, relative to the total weight of the composition.

7. The composition according to claim 6, wherein the at least one compound is present in an amount ranging from 0.005% to 6% by weight, relative to the total weight of the composition.

8. The composition according to claim 1, wherein the composition has a pH ranging from 3 to 12.

9. The composition according to claim 8, wherein the composition has a pH ranging from 5 to 11.

10. The composition according to claim 1, wherein the composition is provided in the form of a composition for the direct dyeing of fibers, and further comprises at least one additional direct dye.

11. The composition according to claim 10, wherein the at least one additional direct dye is chosen from nitrobenzene dyes.

12. The composition according to claim 11, wherein the at least one additional direct dye is chosen from azo dyes, anthraquinone dyes, naphthoquinone dyes, benzoquinone dyes, indigoid dyes, and triarylmethane-based dyes.

13. The composition according to claim 10, wherein the at least one additional direct dye is chosen from nonionic, cationic, and anionic direct dyes.

14. The composition according to claim 10, wherein the at least one additional direct dye is present in an amount ranging from 0.0005% to 12% by weight, relative to the total weight of the composition.

15. The composition according to claim 14, wherein the at least one additional direct dye is present in an amount ranging from 0.005% to 6% by weight, relative to the total weight of the composition.

16. The composition according to claim 1, wherein the composition is a composition for oxidation dyeing and further comprises at least one oxidation base chosen from para- phenylenediamines, bis(phenyl)alkylenediamines, para-aminophenols, ortho-aminophenols, heterocyclic bases, and addition salts thereof with an acid or with an alkaline agent.

17. The composition according to claim 16, wherein the at least one oxidation base is present in an amount ranging from 0.0005% to 12% by weight, relative to the total weight of the composition.

18. The composition according to claim 17, wherein the at least one oxidation base is present in an amount ranging from 0.005% to 6% by weight, relative to the total weight of the composition.

19. The composition according to claim 16, further comprising at least one coupler chosen from meta-phenylenediamines, meta-aminophenols, meta-diphenols, heterocyclic couplers, and addition salts thereof with an acid or with an alkaline agent.

20. The composition according to claim 19, wherein the at least one coupler is present in an amount ranging from 0.0001% to 10% by weight, relative to the total weight of the composition.

21. The composition according to claim 20, wherein the at least one coupler is present in an amount ranging from 0.005% to 5% by weight, relative to the total weight of the composition.

22. The composition according to claim 1, further comprising at least one oxidizing agent.

23. The composition according to claim 22, wherein the at least one oxidizing agent is chosen from hydrogen peroxide, urea peroxide, alkali metal bromates, persalts, and enzymes.

24. The composition according to claim 23, wherein the persalts are chosen from perborates and persulfates.

25. The composition according to claim 23, wherein the enzymes are chosen from peroxidases and two-electron and four-electron oxidoreductases.

26. The composition according to claim 22, wherein the at least one oxidizing agent is hydrogen peroxide.

27. A method for manufacturing a composition for dyeing keratin fibers comprising including in the composition, in an appropriate medium, at least one compound chosen from pyrazine derivatives of formula (I) and addition salts thereof with an acid or alkaline agent:

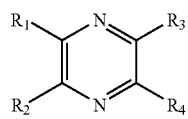
(I)

wherein:
- $R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;
- $R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;
- X is chosen from a hydrogen atom, alkyl radicals, and ions derived from an alkali, alkaline-earth metal, organic amine, or ammonium ions; and
- Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms, and wherein the at least one compound is present in an amount effective for direct dying and/or optical bleaching of the keratin fibers.

28. The method according to claim 27, wherein the keratin fibers are human keratin fibers.

29. A method for dyeing and/or optical bleaching of keratin fibers, comprising:
applying to the fibers at least one composition comprising, in an appropriate medium, at least one compound chosen from pyrazine derivatives of formula (I) and addition salts thereof with an acid or alkaline agent:

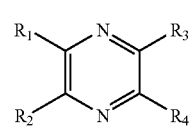
(I)

wherein:
- $R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;
- $R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;
- X is chosen from a hydrogen atom, alkyl radicals, and ions derived from an alkali, alkaline-earth metal, organic amine, or ammonium ions; and
- Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms;

leaving the at least one composition on the fibers for a time period sufficient to develop the desired coloration or optical bleaching;

rinsing the fibers;

optionally washing the fibers with shampoo and rinsing the fibers; and drying the fibers.

30. The method according to claim 29, wherein the keratin fibers are human keratin fibers.

31. A method for dyeing and/or optical bleaching of keratin fibers comprising, applying to the fibers for a time period that is sufficient to develop the desired coloration and/or optical bleaching without final rinsing, at least one composition comprising, in an appropriate medium, at least one compound chosen from pyrazine derivatives of formula (I) and addition salts thereof with an acid or alkaline agent:

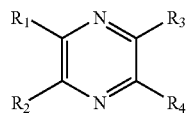

wherein:
R₁ and R₂, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

R₃ and R₄, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of R₁, R₂, R₃, and R₄ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms.

32. The method according to claim 31, wherein the keratin fibers are human keratin fibers.

33. A method for dyeing keratin fibers comprising applying to the fibers, in the absence of oxidation bases and of couplers, at least one composition comprising, in an appropriate medium,
at least one oxidizing agent and
at least one compound chosen from pyrazine derivatives of formula (I) and addition salts thereof with an acid or alkaline agent:

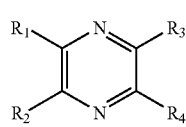

wherein:
R₁ and R₂, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

R₃ and R₄, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of R₁, R₂, R₃, and R₄ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms.

34. The method according to claim 33, wherein the keratin fibers are human keratin fibers.

35. A method for dyeing keratin fibers comprising:
separately storing
(a) at least one oxidizing composition comprising at least one oxidizing composition comprising, in a medium suitable for dyeing, at least one oxidizing agent and
(b) at least one composition comprising, in a medium suitable for dyeing, at least one compound chosen from pyrazine derivatives of formula (I) and addition salts thereof with an acid or alkaline agent:

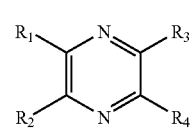

wherein:
R₁ and R₂, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

R₃ and R₄, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms;

mixing the at least one composition and the at least one oxidizing composition together at the time of use;

applying the mixture to the fibers leaving the mixture on the fibers for a time period that is sufficient to develop the desired coloration;

rinsing the fibers;

optionally washing the fibers with shampoo and rinsing the fibers; and drying the fibers.

36. The method according to claim 35, wherein the keratin fibers are human keratin fibers.

37. A method for dyeing keratin fibers comprising applying to the fibers at least one composition comprising, in an appropriate medium, (a) at least one compound chosen from pyrazine derivatives of formula (I) and addition salts thereof with an acid or alkaline agent:

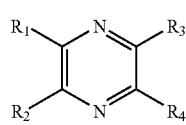

(I)

wherein $R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

$R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms; and (b) at least one oxidation base chosen from para- phenylenediamines, bis(phenyl)alkylenediamines, para-aminophenols, ortho-aminophenols, heterocyclic bases, and addition salts thereof with an acid or with an alkaline agent.

38. The method according to claim 37, wherein said at least one composition applied to the keratin fibers further comprises at least one coupler chosen from meta-phenylened iamines, meta-aminophenols, meta-diphenols, heterocyclic couplers, and addition salts thereof with an acid or with an alkaline agent.

39. The method according to claim 37, wherein said at least one composition applied to the keratin fibers further comprises at least one oxidizing agent.

40. The method according to claim 37, wherein the keratin fibers are human keratin fibers.

41. A method for dyeing keratin fibers comprising, separately storing, (a) at least one composition (A) comprising, in a medium suitable for dyeing, at least one oxidation base and at least one compound chosen from pyrazine derivatives of formula (I) and addition salts thereof with an acid or alkaline agent:

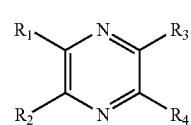

(I)

wherein:

$R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

$R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms, and (b) at least one composition (B) comprising, in a medium that is suitable for dyeing, at least one oxidizing agent;

mixing the at least one composition (A) and the at least one composition (B) together at the time of use;

applying the mixture to the fibers leaving the mixture on the fibers for a time period that is sufficient to develop the desired coloration;

rinsing the fibers;

optionally washing the fibers with shampoo and rinsing the fibers; and drying the fibers.

42. The method according to claim 41, wherein the keratin fibers are human keratin fibers.

43. A multicompartment device for dyeing and/or optical bleaching of keratin fibers comprising, at least one compartment comprising at least one composition comprising, in an appropriate medium, at least one compound chosen from pyrazine derivatives of formula (I) and addition salts thereof with an acid or alkaline agent:

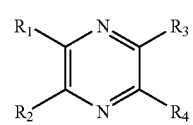

wherein:
$R_1$ and $R_2$, which may be identical or different, are each chosen from a hydrogen atom, a cyano radical, a hydroxyl radical, alkyl radicals, alkenyl radicals, alkoxy radicals, halogen atoms, amino radicals, radicals NRaRb, COOX radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRcRd;

$R_3$ and $R_4$, which may be identical or different, are each chosen from a hydroxyl radical, a cyano radical, halogen atoms, amino radicals, radicals NReRf, COOX radicals, alkyl radicals, alkenyl radicals, alkoxy radicals, or form, together with the two carbon atoms of the pyrazine ring carrying them, a mono- or polycyclic heterocycle comprising at least one heteroatom which is optionally substituted with at least one entity chosen from alkyl radicals, aryl radicals, cyano radicals, halogen atoms, amino radicals, and radicals NRgRh, it being possible for the alkyl, alkoxy and alkenyl radicals of $R_1$, $R_2$, $R_3$, and $R_4$ to be substituted with at least one entity chosen from hydroxyl radicals, amino radicals, aryl radicals, and monocyclic and fused heterocycles;

X is chosen from a hydrogen atom, alkyl radicals, and ions derived from an alkali, alkaline-earth metal, organic amine, or ammonium ions; and Ra, Rb, Rc, Rd, Re, Rf, Rg and Rh, which may be identical or different, are each chosen from alkyl and aryl radicals, or form, with the nitrogen atom carrying them, a 5- or 6-membered heterocycle which may comprise at least one heteroatom, and which may be substituted with at least one entity chosen from alkyl radicals, aryl radicals, and halogen atoms and at least one other compartment comprising at least one oxidizing composition comprising, in an appropriate medium, at least one oxidizing agent.

* * * * *

UNITED STATES PATENT AND TRADEMARK OFFICE
CERTIFICATE OF CORRECTION

| | |
|---|---|
| PATENT NO. | : 7,276,086 B2 |
| APPLICATION NO. | : 10/490860 |
| DATED | : October 2, 2007 |
| INVENTOR(S) | : Luc Gourlaouen |

It is certified that error appears in the above-identified patent and that said Letters Patent is hereby corrected as shown below:

In claim 35, column 17, line 28, "fibers" should read --fibers;--.

In claim 38, column 18, lines 28-29, "meta-phenylened iamines," should read --meta-phenylenediamines,--.

Signed and Sealed this

Eleventh Day of December, 2007

JON W. DUDAS
*Director of the United States Patent and Trademark Office*